United States Patent
Akao et al.

(10) Patent No.: US 8,421,860 B2
(45) Date of Patent: Apr. 16, 2013

(54) INSPECTION METHOD OF HONEYCOMB STRUCTURE

(75) Inventors: Takayoshi Akao, Nagoya (JP); Akihiro Mizutani, Ichinomiya (JP); Kensuke Tanaka, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 524 days.

(21) Appl. No.: 12/718,240

(22) Filed: Mar. 5, 2010

(65) Prior Publication Data

US 2010/0238284 A1 Sep. 23, 2010

(30) Foreign Application Priority Data

Mar. 23, 2009 (JP) .................................. 2009-069370
Feb. 5, 2010 (JP) .................................. 2010-023751

(51) Int. Cl.
*H04N 7/18* (2006.01)

(52) U.S. Cl.
USPC ........................................................ 348/135

(58) Field of Classification Search .................... 348/135
See application file for complete search history.

(56) References Cited

U.S. PATENT DOCUMENTS

| 7,366,340 B1 * | 4/2008 | Smithgall | 382/141 |
| 8,234,909 B2 * | 8/2012 | Suman et al. | 73/38 |
| 2007/0238191 A1 * | 10/2007 | Gargano et al. | 436/164 |

FOREIGN PATENT DOCUMENTS

JP 04-043767 A1 10/1992

* cited by examiner

*Primary Examiner* — Sath V Perungavoor
*Assistant Examiner* — Jeffery Williams
(74) *Attorney, Agent, or Firm* — Burr & Brown

(57) ABSTRACT

An inspection method of a honeycomb structure comprising the steps of illuminating one end face of a honeycomb structure as an inspection target by a light source; condensing, by a condensing lens as a lens having an angle of view, light which is emitted from the light source to the one end face, passed through cells of the honeycomb structure and radiated from the other end face; receiving the light condensed on the condensing lens by a camera; subjecting the light received by the camera to image processing by an image processor, thereby specifying the radiated position of the light on the other end face; and calculating the tilt of the cells of the honeycomb structure from the radiated position of the light on the other end face, and the direction of the tilt.

4 Claims, 5 Drawing Sheets

INSPECTION METHOD OF HONEYCOMB STRUCTURE

BACKGROUND OF THE INVENTION

1. Field of the Invention

The present invention relates to an inspection method of a honeycomb structure. More particularly, it relates to an inspection method of a honeycomb structure which can measure the tilt of cells of the honeycomb structure in a short time without damaging any work (the honeycomb structure).

2. Description of the Related Art

In various fields of chemistry, electric power, iron and steel and the like, a ceramic honeycomb structure which is excellent in heat resistance and corrosion resistance is employed as a carrier for a catalyst device and a filter used for an environmental countermeasure, the collection of a specific material or the like. The honeycomb structure is a cylindrical structure having partition walls which partition a plurality of cells extending through the structure from one end face to the other end face thereof.

In such a honeycomb structure, the central axis of the structure is preferably parallel to a direction in which the cells extend. When the central axis of the honeycomb structure is not parallel to the cell extending direction, the ends of the cells positioned around the outer periphery of the structure are closed with an outer peripheral wall, and the number of the cells having both ends opened decreases sometimes. In this case, there occurs, for example, a problem that a filter area decreases.

To solve the problem, a method for measuring the tilt of the cells is disclosed (e.g., JP-U-4-43767).

SUMMARY OF THE INVENTION

A method for measuring the tilt of cells disclosed in JP-U-4-43767 is based on an assumption that the tilt of the outer peripheral portion of a honeycomb structure is equal to that of each internal cell, and hence the tilt cannot be inspected in a case where the only internal cells tilt. Therefore, in a honeycomb structure having a central axis thereof which is not parallel to a cell extending direction, thereby decreasing a filter area, the tilt cannot be detected. Moreover, in a method for measuring the tilt of the internal cells based on the amount of penetration, the tilt can be measured, but a tilt direction cannot be measured. Furthermore, in a method by CT scanning, there is a problem that efficient measurement for a short time cannot be expected.

The present invention has been developed in view of the above problems, and an object thereof is to provide an inspection method of a honeycomb structure which can efficiently measure the tilt and tilt direction of cells of the honeycomb structure.

To achieve the above object, according to the present invention, an inspection method of a honeycomb structure is provided as follows.

According to a first aspect of the present invention, the inspection method of a honeycomb structure, in which the honeycomb structure which is cylindrical and has porous partition walls to partition a plurality of cells extending through the honeycomb structure from one end face to the other end face thereof is an inspection target is provided, the method comprising the steps of: illuminating the one end face of the honeycomb structure as the inspection target by a light source; condensing, by a lens having an angle of view, light which is emitted from the light source to the one end face, passed through the cells of the honeycomb structure and radiated from the other end face; receiving the light condensed on the condensing lens by a camera; subjecting the light received by the camera to image processing by an image processor, thereby specifying the radiated position of the light on the other end face; and calculating the tilt of the cells of the honeycomb structure from the radiated position of the light on the other end face, and the direction of the tilt.

According to a second aspect of the present invention, the inspection method of the honeycomb structure according to the first aspect is provided, wherein a relation between the angle of the cell extending direction of the honeycomb structure and the radiated position of the light on the other end face of the honeycomb structure is beforehand measured as a relation between a cell angle and the radiated position with respect to a straight line connecting the center of the condensing lens to the focus of the condensing lens, and the radiated position of the light on the other end face of the honeycomb structure as the inspection target is compared with the relation between the cell angle and the radiated position to calculate the tilt of the cells of the honeycomb structure as the inspection target, and the direction of the tilt.

According to the third aspect of the present invention, the inspection method of the honeycomb structure according to the first or second aspects is provided, wherein the light emitted from the light source to the one end face of the honeycomb structure is the light which spreads at a specific radiation angle, and the radiation angle has a size which is not less than the maximum tilt presumed as the tilt of the cells of the honeycomb structure.

According to the fourth aspect of the present invention, the inspection method of the honeycomb structure according to the third aspect is provided, wherein the radiation angle has a size of 10° or less.

According to the inspection method of a plugged honeycomb structure of the present invention, the light transmitted through porous plugged portions of the plugged honeycomb structure is condensed by the lens having the angle of view, the condensed light is received by the camera, and the radiated position of the light on the other end face of the plugged honeycomb structure is specified by the image processing, to calculate the tilt of the cells from the radiated position of the light, whereby the tilt and tilt direction of the cells can be measured in a short time without damaging the work.

DESCRIPTION OF REFERENCE NUMERALS

Figure 1:
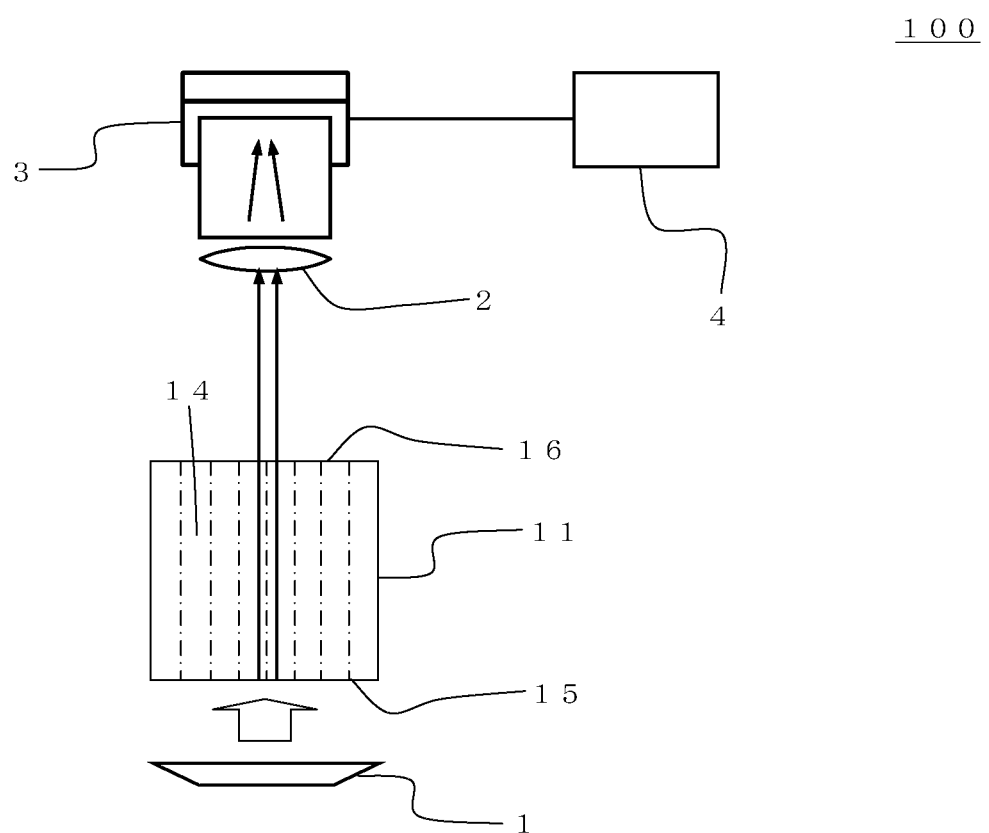
FIG. 1 is a schematic diagram showing that one embodiment of an inspection method of a honeycomb structure of the present invention is performed by using an inspection device of the honeycomb structure.

1: light source, 2: condensing lens, 3: camera, 4: image processor, 11: honeycomb structure, 12: partition wall, 14: cell, 15: one end face, 16: other end face, 21, 22 and 23: image pickup light, Xa: distance from center of image pickup light, x: x-direction, y: y-direction, $\alpha$: radiation angle, $\beta$: spread angle of light emitted from light source, and 100: inspection device of honeycomb structure.

DETAILED DESCRIPTION OF THE INVENTION

Next, an embodiment of the present invention will be described in detail with reference to the drawing, but it should be understood that the present invention is not limited to the following embodiment and that alteration, improvement and the like of design are appropriately added based on the ordinary knowledge of a person with ordinary skill in the art without departing from the scope of the present invention.

Figure 3A:
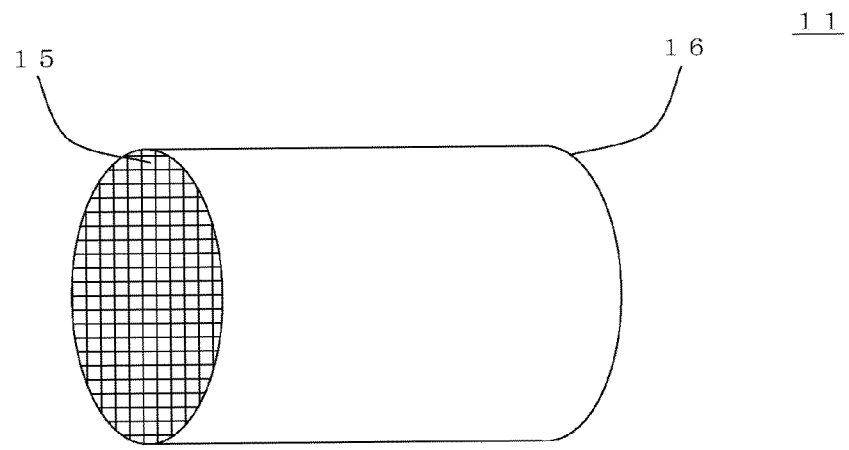
FIG. 3A is a perspective view schematically showing the honeycomb structure as an inspection target of the inspection method of the honeycomb structure of the present invention.
Figure 3B:
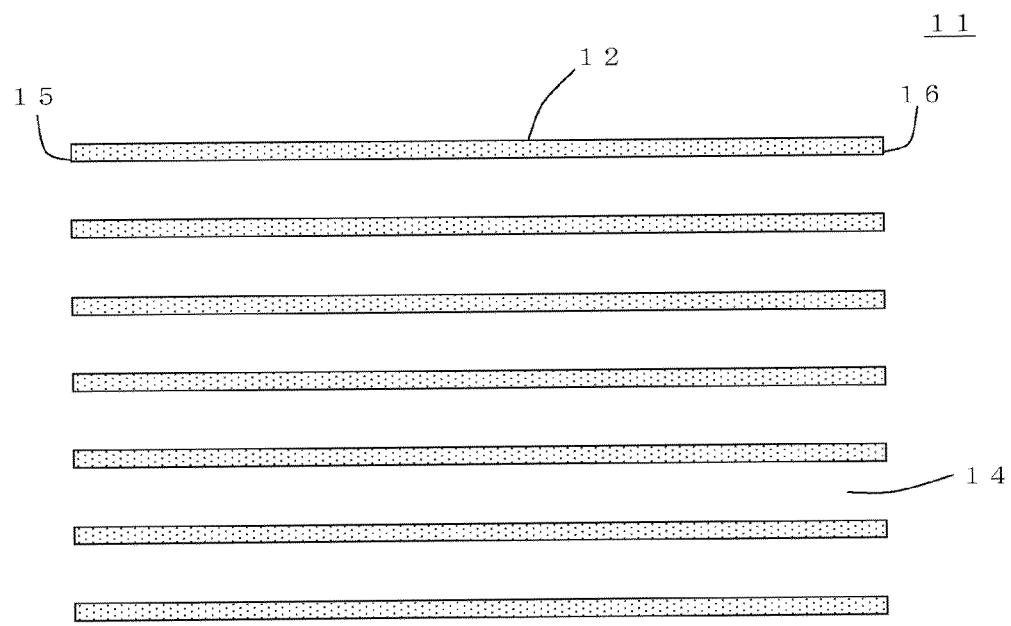
FIG. 3B is a schematic diagram schematically showing a part of the honeycomb structure which is the inspection target of the inspection method of the honeycomb structure of the present invention, that is, showing the cross section of the honeycomb structure parallel to a central axis thereof.

1. Honeycomb Structure:

In one embodiment of an inspection method of a honeycomb structure of the present invention, as shown in FIGS. 3A and 3B, the honeycomb structure having porous partition walls 12 which partition a plurality of cells 14 extending through the honeycomb structure from one end face 15 to the other end face 16 thereof is an inspection target, and the honeycomb structure having a radius of a cross section (a round cross section) thereof disposed perpendicularly to a central axis direction thereof in a range of 50 to 500 mm and having a length thereof along the central axis direction in a range of 40 to 500 mm is preferably the inspection target (there is not any special restriction on the shape of the cross section, and the shape may be, for example, an elliptic, quadrangular or triangular shape or the like). The honeycomb structure as the inspection target is preferably made of a ceramic material, and is preferably made of, for example, cordierite, silicon carbide (SiC), Si—SiC or the like. The honeycomb structure manufactured by a known method may be the inspection target. Moreover, in the honeycomb structure which is the inspection target of the inspection method of the honeycomb structure of the present embodiment, an angle $\theta'$ formed by a central axis direction and a cell extending direction is preferably not more than the angle of view of a condensing lens 2. If the angle exceeds the angle of view of the condensing lens 2, a cell angle of the honeycomb structure as the inspection target cannot be measured. Moreover, the honeycomb structure as the inspection target may be a plugged honeycomb structure in which plugged portions are formed in open frontal areas of predetermined cells in the one end face and open frontal areas of the remaining cells in the other end face. Here, FIG. 3A is a perspective view schematically showing the honeycomb structure which is the inspection target of the inspection method of the honeycomb structure of the present invention. FIG. 3B is a schematic diagram schematically showing a part of the honeycomb structure which is the inspection target of the inspection method of the honeycomb structure of the present invention, that is, showing the cross section of the honeycomb structure parallel to the central axis thereof.

2. Inspection Method of Honeycomb Structure:

The embodiment of the inspection method of the honeycomb structure of the present invention is a method for measuring the tilt and tilt direction of the cells of the plugged honeycomb structure by use of, for example, an inspection device 100 of the honeycomb structure shown in FIG. 1. In the inspection method of the plugged honeycomb structure of the present embodiment, a cylindrical honeycomb structure 11 having porous partition walls which partition a plurality of cells 14 extending the honeycomb structure from one end face 15 to the other end face 16 thereof is the inspection target. The inspection device illuminates the one end face (the end face directed on the side of a light source) 15 with a light source 1, condenses the light emitted from the light source 1 to the one end face 15, passed through the cells of the honeycomb structure 11 and radiated from the other end face (the end face facing the side of the condensing lens) 16 by the lens 2 having an angle of view, receives the light condensed on the condensing lens 2 by a camera 3, subjects the light received by the camera 3 to image processing by an image processor 4, and specifies the radiated position of the light on the other end face 16 to calculate the tilt of the cells 14 of the honeycomb structure 11 from the radiated position of the light on the other end face 16. FIG. 1 is a schematic diagram showing that the embodiment of the inspection method of the honeycomb structure of the present invention is performed by use of the inspection device 100 of the honeycomb structure.

According to the inspection method of the honeycomb structure of the present embodiment, the light transmitted through the cells of the honeycomb structure is condensed by the lens having the angle of view, the condensed light is received by the camera, and the radiated position of the light on the other end face of the honeycomb structure is specified by the image processing, to calculate the tilt and tilt direction of the cells from the radiated position of the light, whereby the tilt and tilt direction of the cells can efficiently be measured. Here, "measure the tilt of the cells" means that the angle of the cells with respect to the central axis of the honeycomb structure is measured. Moreover, "measure the direction of the tilt of the cells" means that the direction in which the cells tilt from the central axis of the honeycomb structure (the tilting direction) is measured.

In the inspection method of the honeycomb structure of the present embodiment, since the light passed through the cells of the honeycomb structure is condensed by the lens having the angle of view, in the light radiated from the other end face of the honeycomb structure, the only light emitted to the condensing lens and formed into an image by a light receiving element is received by the camera, whereby the position of the light on the other end face of the honeycomb structure can be grasped. Therefore, in a case where the cells of the honeycomb structure are parallel to the central axis thereof, when the condensing lens 2 and the honeycomb structure 11 are disposed so that a straight line connecting the center of the condensing lens 2 to the focus of the condensing lens 2 matches (becomes the same straight line as) the central axis of the honeycomb structure, as shown in FIG. 1, the light transmitted through the cells near the central axis of the honeycomb structure 11 is emitted to the condensing lens 2, and formed into the image in the center of the light receiving element, whereby the light radiated from the center of the other end face 16 of the honeycomb structure 11 is observed (see image pickup light 21 of FIG. 4). That is, when the central axis of the honeycomb structure is parallel to the cells, the light is observed which is radiated from a portion where the straight line connecting the center of the condensing lens 2 to the focus of the condensing lens 2 crosses the other end face of the honeycomb structure. In this case, the image obtained from the light received by the camera is an image in which the center of the other end face 16 of the plugged honeycomb structure 11 shines. A range of the light observed as the image pickup light on the other end face of the plugged honeycomb structure is determined by the angle of view of the condensing lens.

Figure 2:
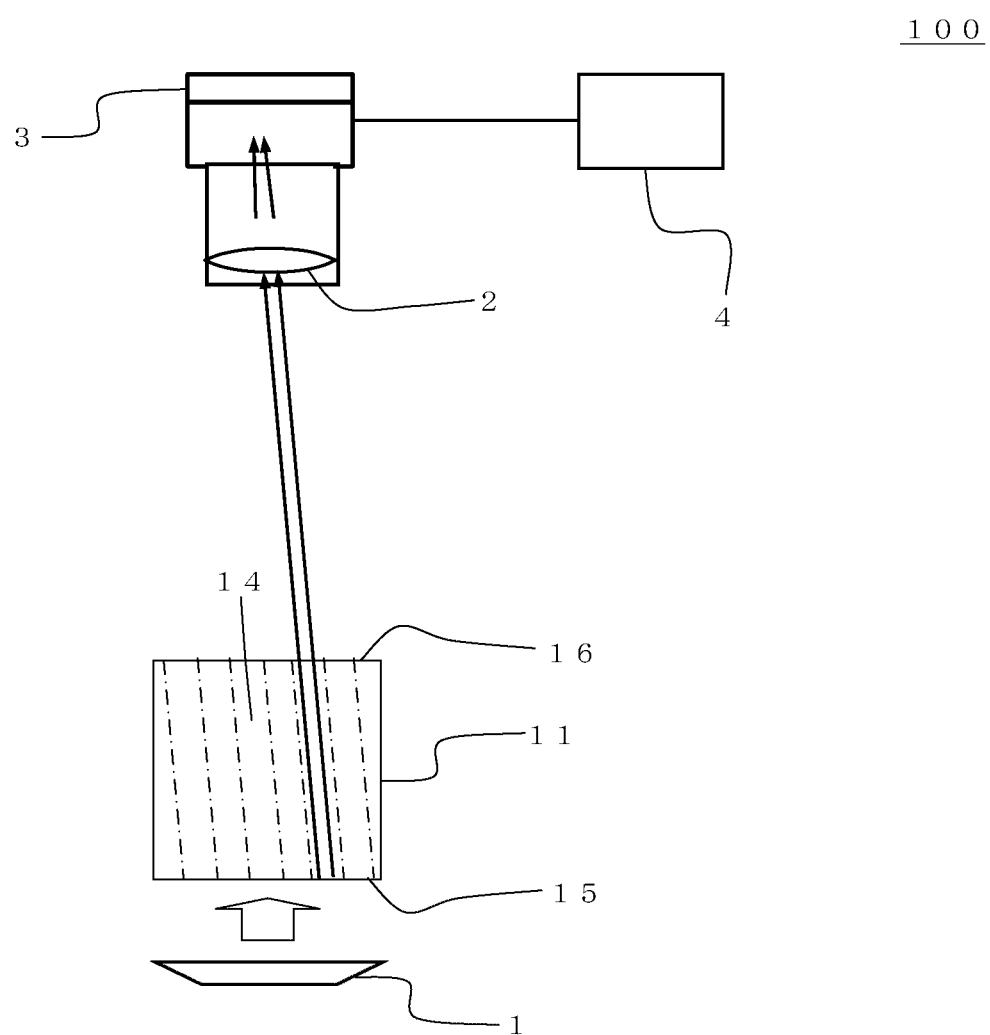
FIG. 2 is a schematic diagram showing that the embodiment of the inspection method of the honeycomb structure of the present invention is performed by using the inspection device of the honeycomb structure.

Moreover, as shown in FIG. 2, when the cells 14 of the honeycomb structure 11 tilt (when the cells 14 are not parallel to the central axis of the honeycomb structure 11), the light which is emitted to the condensing lens 2 and formed into the image by the light receiving element is not the light which is transmitted through the cells around the central axis of the honeycomb structure, but is the light which is transmitted through the cells at positions shifted a little toward an outer peripheral side form the central axis of the honeycomb structure. Therefore, when the cells 14 of the honeycomb structure 11 tilt, the light radiated from the position shifted a little toward the outer peripheral side from the center of the other end face 16 of the honeycomb structure 11 (a portion where the straight line connecting the center of the condensing lens 2 to the focus of the condensing lens 2 intersects with the other end face of the honeycomb structure) (see image pickup light 22 of FIG. 5). Here, FIG. 2 is a schematic diagram showing the embodiment of the inspection method of the honeycomb structure of the present invention is performed by using the inspection device 100 of the honeycomb structure. The light transmitted through the cells other than "the cells at the positions shifted a little from the central axis to the outer peripheral side" of the above honeycomb structure is emitted to the condensing lens 2, and is not formed into the image by the light receiving element, whereby the light is not received by the camera. When the cells of the honeycomb structure tilt in this manner, the light transmitted through the cells at the positions shifted a little from the central axis of the honeycomb structure to the outer peripheral side thereof is received by the camera. Therefore, when the position of the light on the other end face of the honeycomb structure is shifted from the central axis in the image formed by the light received by the camera, the cells of the honeycomb structure tilt. Moreover, when the shift of the position of the light is two-dimensionally acquired, the direction of the tilt can be known.

Moreover, in the inspection method of the honeycomb structure of the present embodiment, a relation between the angle of the cell extending direction of the honeycomb structure with respect to the straight line connecting the center of the condensing lens and the focus thereof and the radiated position of the light on the other end face of the honeycomb structure is obtained as "a relation between a cell angle and the radiated position", and the "relation between the cell angle and the radiated position" is beforehand measured. The radiated position of the light on the other end face of the honeycomb structure as the inspection target is preferably compared with the "relation between the cell angle and the radiated position" to calculate the tilt of the cells of the honeycomb structure as the inspection target. Here, the "radiated position of the light on the other end face of the honeycomb structure" is the position of the center of the range of the light on the other end face of the honeycomb structure. The above "center" is the center of a circle in a case where the range of the light is round, an intersection between a long diameter and a short diameter in a case where the range of the light is elliptic, or a position corresponding to a gravity point in a case where the range of the light has another shape. The "relation between the cell angle and the radiated position" is preferably obtained, for example, by disposing the honeycomb structure so that one end face and the other end face are disposed perpendicularly to the central axis and so that the cell extending direction is the central axis direction and so that the central axis of the honeycomb structure matches the straight line (the enter line of the condensing lens) connecting the center of the condensing lens to the focus thereof; and measuring the radiated position of the light on the other end face of the honeycomb structure while tilting the honeycomb structure little by little from this state to vary the angle formed by the cell extending direction of the honeycomb structure and the center line of the condensing lens. Further specifically, the "relation between the cell angle and the radiated position" is preferably measured by first observing the radiated position of the light on the other end face of the honeycomb structure in a state in which the central axis of the honeycomb structure matches the center line of the condensing lens; observing the radiated position of the light on the other end face of the honeycomb structure in a state in which the central axis of the honeycomb structure tilts as much as 1.0° (this angle may be a desired angle) from the center line of the condensing lens; and observing the radiated position of the light on the other end face of the honeycomb structure while successively increasing the angle formed by the central axis of the honeycomb structure and the center line of the condensing lens as much as 1.0° (this angle may be a desired angle). The range of the "cell angle" during the measurement of the "relation between the cell angle and the radiated position" is determined by the angle of view of the condensing lens, and the light radiated from the other end face of the honeycomb structure can preferably be measured in the range of the cell angle. In this case, when the light radiated from the other end face of the honeycomb structure as the inspection target cannot be observed, the tilt angle of the cells of the honeycomb structure as the inspection target is larger than the maximum value of the above range of the cell angle.

In the inspection method of the honeycomb structure of the present embodiment, the light source 1 is disposed at such a position as to illuminate the one end face 15 of the honeycomb structure 11, and a distance between the light source and the one end face of the honeycomb structure is preferably 0 mm. The distance may be longer than 0 mm, but problems occur that a mechanism for supporting the honeycomb structure needs to be separately provided and that a ratio S/N decreases owing to the decrease of the amount of the light.

In the inspection method of the honeycomb structure of the present embodiment, the condensing lens 2 needs to be a lens having an angle of view. When the honeycomb structure is disposed between the condensing lens 2 and the light source 1, the condensing lens 2 is preferably focused on the one end face (the end face facing the side of the light source) 15 of the honeycomb structure 11. Moreover, a distance between the condensing lens 2 and the other end face (the end face facing the side of the condensing lens) 16 is preferably from 40 to 2000 mm. As the distance is shorter in this range, the cell tilt can be measured in a limited range, and an inspectable tile range broadens. On the other hand, as the distance between the condensing lens 2 and the other end face (the end face facing the side of the condensing lens) 16 is longer, the inspectable tilt range narrows, but the cell tilt in a large range can be measured, and the number of inspection times can be decreased. If the distance is excessively short, the honeycomb structure comes in contact with the condensing lens 2, and the condensing lens 2 might break down. If the distance is excessively long, the size of a device becomes excessively large.

3. Inspection Device of Honeycomb Structure:

The inspection method of the honeycomb structure of the present invention is preferably performed by using an inspection device of the honeycomb structure as follows.

As shown in FIG. 1, the inspection device 100 of the honeycomb structure used in the inspection method of the honeycomb structure of the present invention preferably comprises the light source 1 which illuminates the one end face (the end face facing the light source side) 15 of the honeycomb structure 11 as the inspection target; the condensing lens 2 for condensing the light which is emitted from the light source 1 to the one end face 15, passed through the cells of the honeycomb structure 11 and radiated from the other end face (the end face facing the condensing lens side) 16; the camera 3 which receives data of the light condensed by the condensing lens 2; and the image processor 4 which subjects the light received by the camera 3 to image processing to display the contrast (luminance) of the light passed through the cells of the honeycomb structure 11. An arrow directed from the light source to the camera as shown in FIG. 1 indicates the proceeding of the light, and this also applies to FIG. 2.

In the inspection device 100 of the honeycomb structure, as the light source, a brighter diffusion light source is preferably used so as to keep uniform illuminance in a plane and to detect a faint signal.

Figure 7:
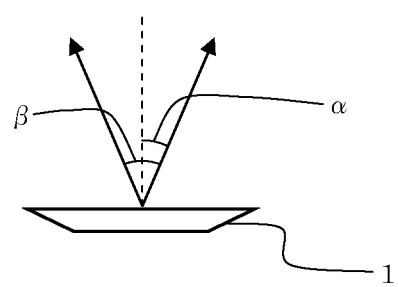
FIG. 7 is a schematic diagram showing the spread of the light emitted from a light source.

Moreover, the light emitted from the light source 1 to the one end face of the honeycomb structure is the light which spreads at a specific radiation angle α, and the radiation angle α has a size which is not less than "the maximum tilt (angle) θ presumed as the tilt of the cells of the honeycomb structure (the presumed maximum cell tilt)". Since the angle (the radiation angle) of the light emitted from the light source is such an angle, the light from the light source securely passes through the cells which tilt as much as the angle θ, and hence the tilt of the cells of the honeycomb structure can more securely be measured. If the radiation angle α is smaller than the presumed maximum cell tilt θ", the light from the light source cannot securely pass through the cells which tilt as much as the angle θ, and hence the tilt of the cells of the honeycomb structure is not easily measured sometimes. Here, the presumed maximum cell tilt θ" is an angle of 120% of the maximum tilt in an allowable range (a standard range) of a cell tilt θ1 of the manufactured honeycomb structure. The cell tilt θ is obtained by measuring, with a gauge, the cell tilt of the honeycomb structure cut along a plane including the central axis of the honeycomb structure. For example, in the honeycomb structure prepared by extruding a ceramic material, followed by drying and firing, the "presumed maximum cell tilt θ" is specifically 5.0°. The "radiation angle α" of the light from the light source is an angle having a size of ½ of the spread angle β of the light emitted from the light source 1 as shown in FIG. 7. FIG. 7 is a schematic diagram showing the spread of the light emitted from the light source 1. In FIG. 7, "arrows" indicate the light emitted from the light source 1.

Furthermore, the radiation angle α is preferably 10° or less. Moreover, the radiation angle α is further preferably equal to the maximum cell tilt (the presumed maximum cell tilt θ). When the radiation angle α has such a size, the intensity of the light from the light source does not weaken, and hence the cell tilt of the honeycomb structure can more securely be measured. If the radiation angle α is larger than 10°, the light from the light source excessively spreads, and the intensity of the light weakens, whereby the tilt of the cells of the honeycomb structure is not easily measured sometimes.

In the inspection device 100 of the honeycomb structure, the condensing lens 2 is a lens having an angle of view, and condenses the light emitted from the light source 1 and passed through the cells of the honeycomb structure 11 toward the camera 3. The condensing lens needs to have an angle of view which is not less than the "cell angle" to be measured.

In the inspection device 100 of the honeycomb structure, the camera 3 preferably has a high sensitivity. The camera 3 has a function of receiving the light condensed by the condensing lens 2 and sending data of the received light to the image processor.

In the inspection device 100 of the honeycomb structure, the image processor 4 preferably comprises a display unit in which the picked image can be displayed. Alternatively, the image processor preferably has a function of calculating the contrast (luminance) of the light received by the camera to detect the position of the light radiated from the other end face of the honeycomb structure. Moreover, in addition to the function of detecting the position of the radiated light, the image processor preferably has a function of calculating the cell tilt and tilt direction from the position of the detected light. Furthermore, the image processor preferably has a display unit capable of displaying the picked image and the function of detecting the position of the light. The image processor further preferably has a display unit capable of displaying the picked image, the function of detecting the position of the light, and the function of calculating the cell tilt and tilt direction from the position of the detected light.

EXAMPLES

Hereinafter, the present invention will further specifically be described with respect to examples, but the present invention is not limited to these examples.

Example 1

As shown in FIG. 1, a light source was disposed so as to illuminate the upside in a vertical direction, a condensing lens was disposed at a position of 460 mm from the light source and above the light source in the vertical direction, a camera was disposed at a position of 0 mm from the condensing lens and above the condensing lens in the vertical direction, and the camera was connected to an image processor, thereby obtaining an inspection device of a plugged honeycomb structure. The respective units were fixed to a rack.

As the light source, planar illumination of a fluorescent lamp having a radiation angle α of 10° was used. As the condensing lens, a CCTV lens having a diameter of 35.5 mm, an angle of view of 34.09° and a focal length of 25 mm was used. As the camera, a CCD camera of four million pixels was used. As the image processor, a personal computer was used.

The plugged honeycomb structure prepared by the following method was an inspection target, and the tilt of cells of the structure was measured. Moreover, an analytical curve used for the calculation of the tilt of the cells was prepared as follows. To perform an inspection, the plugged honeycomb structure as the inspection target was disposed at a position of 0 mm above the light source (on the upside in the vertical direction) so that one end face of the structure was directed perpendicularly to the vertical direction and downwards in the vertical direction. The intensity of the light from the light source was set to 80000 lx. The obtained result is shown in Table 1. In Table 1, a "radiated position" indicates a distance from the center (the center of the other end face of the plugged honeycomb structure (the end face facing a condensing lens side) in the unit (pixel) of image processing.

(Preparation of Plugged Honeycomb Structure)

A plurality of materials selected from the group consisting of talc, kaolin, calcinated kaolin, alumina, calcium hydroxide and silica were combined, and blended at predetermined ratio so that the chemical composition of the materials was from 42 to 56 mass % of silica ($SiO_2$), from 30 to 45 mass % of alumina ($Al_2O_3$) and from 12 to 16 mass % of magnesia (MgO), thereby forming a cordierite forming material. To 100 parts by mass of the material, 12 to 25 parts by mass of graphite as a pore former, and 5 to 15 parts by mass of synthetic resin were added. Furthermore, after adding appropriate amounts of methylcellulose and surfactant, respectively, water was added, followed by kneading, whereby a kneaded clay was prepared. After deaerating the prepared kneaded clay in vacuum, the kneaded clay was extruded to obtain a formed honeycomb article. Next, the formed honeycomb article was fired to obtain a fired honeycomb article (a porous base member). Firing conditions were set to 1400 to 1430° C. and ten hours. Next, the obtained fired honeycomb article was plugged. Open frontal areas of cells in one end face of the obtained fired honeycomb article were alternately masked in a checkered pattern, and the end of the article on a masked side was submerged into a plugging slurry containing a cordierite material as a ceramic material, thereby forming plugged portions alternately arranged in the checkered pattern. Furthermore, in the other end of the article, the cells each having the one end thereof plugged were masked, and plugged portions were formed in the same manner as in the above method for forming the plugged portions in the one end of the article. The fired honeycomb article provided with the plugged portions was dried and fired to obtain the plugged honeycomb structure. The obtained plugged honeycomb structure had a cylindrical shape having a bottom surface diameter of 190 mm and a length of 200 mm in a central axis direction, and also had a partition wall thickness of 0.3 mm and a cell density of 31 cells/$cm^2$.

(Preparation of Analytical Curve)

The plugged honeycomb structure was prepared by the above method of the "preparation of the plugged honeycomb structure". When the cell extending direction of the structure was not parallel to the central axis thereof, the outer peripheral surface thereof was ground so that the cell extending direction was parallel to the central axis, if necessary. When both the end faces of the structure did not cross the central axis thereof, both the ends of the structure were cut so that both the end faces were disposed perpendicularly to the central axis, thereby obtaining the plugged honeycomb structure having both the end faces disposed perpendicularly to the central axis and having the cell extending direction which was parallel to the central axis.

Figure 4:
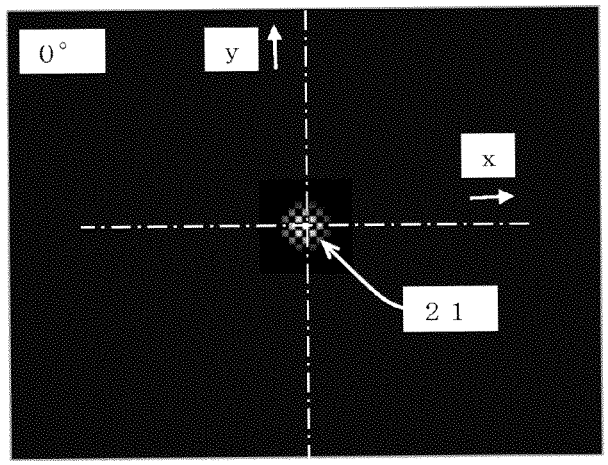
FIG. 4 is a schematic diagram showing a result obtained by performing the inspection method of the honeycomb structure of the present invention while the honeycomb structure is disposed so that the central axis thereof matches the center line of a condensing lens, and showing the state of light passing through cells.
Figure 5:
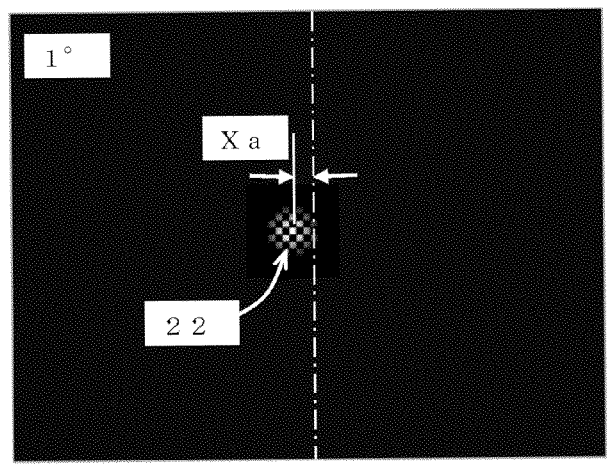
FIG. 5 is a schematic diagram showing a result obtained by performing the inspection method of the honeycomb structure of the present invention while the central axis of the honeycomb structure tilts as much as 1.0° from the center line of the condensing lens, and showing the state of the light passing through the cells.
Figure 6:
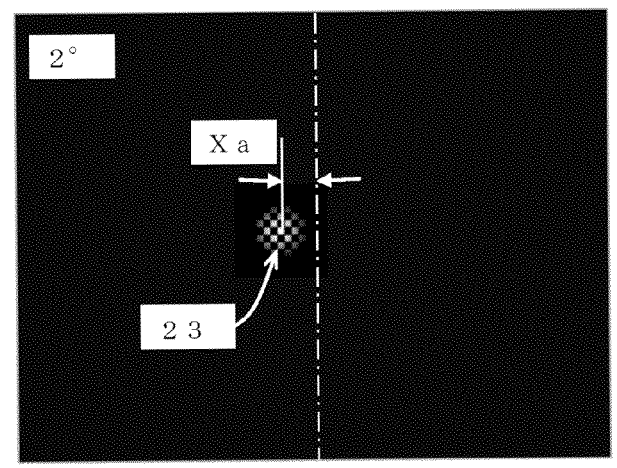
FIG. 6 is a schematic diagram showing a result obtained by performing the inspection method of the honeycomb structure of the present invention while the central axis of the honeycomb structure tilts as much as 2.0° from the center line of the condensing lens, and showing the state of the light passing through the cells.

Moreover, the obtained plugged honeycomb structure was used. The radiated position of the light on the other end face of the plugged honeycomb structure was first observed in a state in which the central axis of the plugged honeycomb structure matched the center line of the condensing lens, and the radiated position of the light on the other end face of the plugged honeycomb structure was observed in a state in which the central axis of the plugged honeycomb structure tilted as much as 1.0° from the center line of the condensing lens. The radiated position of the light on the other end face of the plugged honeycomb structure was observed while successively increasing an angle formed by the central axis of the honeycomb structure and the center line of the condensing lens as much as 1.0°, to measure a "relation between the cell angle and the radiated position". Then, the analytical curve obtained by linearly approximating data of the obtained "relation between the cell angle and the radiated position" by a least-squares method was used. A formula of an obtained straight line (the analytical curve) was "y=−47.457x+823.8, y: a radiated position (pixel), x: the tilt (°) of the cells, and the range of x: 0.0 to 5.0°". The plugged honeycomb structure was not tilted in a y-direction shown by an arrow y in FIG. 4, and tilted only in an x-direction shown by an arrow x. In FIG. 4, an intersection between a one-dot chain line extending in the x-direction and a one-dot chain line extending in the y-direction is the center of the other end face of the plugged honeycomb structure. In FIGS. 5 and 6, Xa is a distance of image pickup light 22 or 23 from the center of the other end face of the plugged honeycomb structure. The result of the "relation between the cell angle and the radiated position" is shown in Table 2 and FIGS. 4 to 6. It is to be noted that in a case where the tilt of the cells of the plugged honeycomb structure as the inspection target is measured, when the observed radiated position (the radiated position of the light on the other end face of the plugged honeycomb structure) shifts from the center (the intersection between the center line of the condensing lens and the other end face of the plugged honeycomb structure) and the shift direction of the radiated position is not parallel to the x-direction or the y-direction, the coordinates of the x-direction and the y-direction can be obtained by image processing to specify the shift direction of the radiated position (the direction of the shift from the center). FIG. 4 is a schematic diagram showing a result obtained by performing the inspection method of the plugged honeycomb structure of the present invention while the plugged honeycomb structure is disposed so that the central axis thereof matches the center line of the condensing lens, and showing the state of the light transmitted through the plugged portions. FIG. 5 is a schematic diagram showing a result obtained by performing the inspection method of the plugged honeycomb structure of the present invention while the central axis of the plugged honeycomb structure tilts as much as 1.0° from the center line of the condensing lens, and showing the state of the light transmitted through the plugged portions. FIG. 6 is a schematic diagram showing a result obtained by performing the inspection method of the plugged honeycomb structure of the present invention while the central axis of the plugged honeycomb structure tilts as much as 2.0° from the center line of the condensing lens, and showing the state of the light transmitted through the plugged portions.

TABLE 1

|  | Radiated position (pixel) | Cell tilt (°) |
|---|---|---|
| Example 1 | 806 | 0.4 |

TABLE 2

| Radiated position (pixel) | Cell tilt (°) |
|---|---|
| 824 | 0.0 |
| 773 | 1.0 |
| 726 | 2.0 |
| 689 | 3.0 |
| 640 | 4.0 |
| 579 | 5.0 |

It is seen from Example 1 that by the inspection method of the honeycomb structure of the present invention, it is possible to measure the tilt angle of the cells of the honeycomb structure in which the cells tilt, and the direction of the tilt.

Examples 2 to 17

An inspection device of a plugged honeycomb structure was prepared in the same manner as in Example 1 except that the radiation angle α of a light source was varied as shown in Table 3 (Examples 2 to 17). There was observed the state (visibility) of image pickup light in a case where the tilt of cells of the honeycomb structure and the direction of the tilt were measured by using the obtained inspection device of the plugged honeycomb structure. It is to be noted that to observe the image pickup light, the plugged honeycomb structure was used in which a cell extending direction was a central axis direction. Subsequently, the plugged honeycomb structure was disposed in a state in which the central axis thereof tilted as much as 0° (γ=0°), 1° (γ=1°), 2° (γ=2°), 3° (γ=3°), 4° (γ=4°) and 5° (γ=5°) in a vertical direction, and the light at the respective angles was observed. It is to be noted that the angle γ is an angle formed by the central axis of the plugged honeycomb structure and the vertical direction (the smaller angle), and is the tilt of the cells in the vertical direction. Moreover, as evaluation in the observation of the image pickup light, "appearance of the image pickup light" was evaluated. A case where the image pickup light could remarkably satisfactorily be observed was evaluated as "A", a case where the image pickup light could satisfactorily be observed was evaluated as "B", and a case where the image pickup light could be observed but a slightly blurred state was observed was evaluated as "C".

TABLE 3

|  | Radiation angle α (°) | Appearance of image pickup light | | | | | |
|---|---|---|---|---|---|---|---|
|  |  | γ = 0° | γ = 1° | γ = 2° | γ = 3° | γ = 4° | γ = 5° |
| Example 2 | 0 | A | C | C | C | C | C |
| Example 3 | 1 | A | A | C | C | C | C |
| Example 4 | 2 | A | A | A | C | C | C |
| Example 5 | 3 | A | A | A | A | C | C |
| Example 6 | 4 | A | A | A | A | A | C |
| Example 7 | 5 | A | A | A | A | A | A |
| Example 8 | 6 | B | B | B | B | B | B |
| Example 9 | 7 | B | B | B | B | B | B |
| Example 10 | 8 | B | B | B | B | B | B |
| Example 11 | 9 | B | B | B | B | B | B |
| Example 12 | 10 | B | B | B | B | B | B |
| Example 13 | 11 | C | C | C | C | C | C |
| Example 14 | 12 | C | C | C | C | C | C |
| Example 15 | 13 | C | C | C | C | C | C |
| Example 16 | 14 | C | C | C | C | C | C |
| Example 17 | 15 | C | C | C | C | C | C |

It is seen from Table 3 that when the radiation angle α is not less than the tilt γ of the cells and the radiation angle α is 5° or less, the image pickup light can remarkably satisfactorily be detected. Moreover, it is seen that when the radiation angle α is larger than 5°, and 10° or less, the image pickup light can satisfactorily be detected. Furthermore, it is seen that when the radiation angle α is smaller than the tilt γ of the cells, the amount of the light decreases, and the image pickup light is slightly blurred. In addition, it is seen that when the radiation angle α exceeds 10°, the amount of the light decreases, and the image pickup light is slightly blurred.

In the inspection method of the honeycomb structure of the present invention, the tilt of the cells can efficiently be measured. Therefore, the method can preferably be utilized in the manufacturing of the honeycomb structure in which the cells tilt less. The obtained honeycomb structure can preferably be utilized as a carrier for a catalyst device used for an environmental countermeasure, the collection of a specific substance or the like, or as a filter in various fields of chemistry, electric power, iron and steel and the like.

What is claimed is:

1. An inspection method of a honeycomb structure, the honeycomb structure which is cylindrical and has porous partition walls to partition a plurality of cells extending through the honeycomb structure from one end face to the other end face thereof is an inspection target, the method comprising the steps of:
    aligning a first end surface of the one end face of the honeycomb structure orthogonally with respect to the optical axis of a light source;
    illuminating the one end face of the honeycomb structure as the inspection target by the light source;
    condensing, by a lens having an angle of view, light which is emitted from the light source to the one end face, passed through the cells of the honeycomb structure and radiated from the other end face;
    receiving the light condensed on the condensing lens by a camera;
    subjecting the light received by the camera to image processing by an image processor, thereby specifying the radiated position of the light on the other end face; and
    calculating the tilt of the cells of the honeycomb structure from the radiated position of the light on the other end face, and the direction of the tilt.

2. The inspection method of the honeycomb structure according to claim 1, wherein a relation between the angle of the cell extending direction of the honeycomb structure and the radiated position of the light on the other end face of the honeycomb structure is beforehand measured as a relation between a cell angle and the radiated position with respect to a straight line connecting the center of the condensing lens to the focus of the condensing lens, and
    the radiated position of the light on the other end face of the honeycomb structure as the inspection target is compared with the relation between the cell angle and the radiated position to calculate the tilt of the cells of the honeycomb structure as the inspection target, and the direction of the tilt.

3. The inspection method of the honeycomb structure according to claim 1, wherein the light emitted from the light source to the one end face of the honeycomb structure is the light which spreads at a specific radiation angle, and the radiation angle has a size which is not less than the maximum tilt presumed as the tilt of the cells of the honeycomb structure.

4. The inspection method of the honeycomb structure according to claim 3, wherein the radiation angle has a size of 10° or less.

* * * * *